US008575202B2

(12) United States Patent
Au et al.

(10) Patent No.: US 8,575,202 B2
(45) Date of Patent: *Nov. 5, 2013

(54) CHELATOR STABILIZED CATIONIC AMMONIUM COMPOUNDS AND COMPOSITIONS COMPRISING THE SAME

(71) Applicants: Van Au, Trumbull, CT (US); Stephen Alan Madison, Trumbull, CT (US)

(72) Inventors: Van Au, Trumbull, CT (US); Stephen Alan Madison, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/669,981

(22) Filed: Nov. 6, 2012

(65) Prior Publication Data
US 2013/0137773 A1 May 30, 2013

Related U.S. Application Data

(63) Continuation of application No. 12/559,850, filed on Sep. 15, 2009, now Pat. No. 8,324,255.

(51) Int. Cl.
*A61K 31/44* (2006.01)
*A61K 31/14* (2006.01)
*C07D 213/78* (2006.01)
*C07C 225/00* (2006.01)

(52) U.S. Cl.
USPC ............ 514/350; 514/642; 546/299; 564/292

(58) Field of Classification Search
USPC .................... 514/350, 642; 546/299; 564/292
See application file for complete search history.

(56) References Cited

U.S. PATENT DOCUMENTS

| | | | |
|---|---|---|---|
| 2,247,017 | A | 5/1930 | Henning |
| 5,202,048 | A | 4/1993 | Bartolo |
| 5,352,438 | A | 10/1994 | N'Guyen et al. |
| 5,552,031 | A | 9/1996 | Moon |
| 5,703,323 | A | 12/1997 | Rothgery |
| 5,900,393 | A | 5/1999 | Ramachandran |
| 6,113,712 | A | 9/2000 | Ciaramitaro |
| 6,645,475 | B2 | 11/2003 | Franklin et al. |
| 7,087,560 | B2 | 8/2006 | McManus |
| 7,175,836 | B1 | 2/2007 | Hart |
| 7,175,837 | B2 | 2/2007 | Schiltz |
| 7,176,172 | B2 | 2/2007 | Harding |
| 7,202,198 | B2 | 4/2007 | Gordon |
| 7,282,471 | B2 | 10/2007 | Harichian et al. |
| 7,425,323 | B2 | 9/2008 | Schiltz |
| 8,257,720 | B2 | 9/2012 | Au et al. |
| 8,324,255 | B2 * | 12/2012 | Au et al. ........................ 514/350 |
| 2001/0047039 | A1 | 11/2001 | McManus |
| 2003/0190302 | A1 | 10/2003 | Frantz |
| 2004/0018244 | A1 | 1/2004 | Piterski |
| 2004/0161402 | A1 | 8/2004 | Brooks |
| 2004/0191205 | A1 | 9/2004 | Evans |
| 2004/0259951 | A1 | 12/2004 | Clarkson |
| 2005/0169879 | A1 | 8/2005 | Glover |
| 2005/0239670 | A1 | 10/2005 | Stella |
| 2005/0288198 | A1 | 12/2005 | Pereira |
| 2006/0045861 | A1 | 3/2006 | Bejger |
| 2006/0046943 | A1 | 3/2006 | Erazo-Majewicz |
| 2006/0088495 | A1 | 4/2006 | Harichian et al. |
| 2006/0089277 | A1 | 4/2006 | Harding et al. |
| 2006/0093634 | A1 | 5/2006 | Lutz |
| 2006/0148757 | A1 | 7/2006 | Oku |
| 2007/0048235 | A1 | 3/2007 | Harmalker et al. |
| 2007/0053853 | A1 | 3/2007 | Hurley et al. |
| 2007/0212324 | A1 | 9/2007 | Harichian |
| 2007/0299284 | A1 | 12/2007 | Deavenport |
| 2008/0145452 | A1 | 6/2008 | Lichtblau |
| 2008/0206351 | A1 | 8/2008 | Yang |
| 2008/0299054 | A1 | 12/2008 | Chandar |
| 2010/0266521 | A1 | 10/2010 | Unilever |
| 2011/0065802 | A1 | 3/2011 | Au |

FOREIGN PATENT DOCUMENTS

| | | |
|---|---|---|
| AU | 442661 | 2/1972 |
| AU | 607664 | 9/1989 |
| AU | 734334 B2 | 10/1999 |
| AU | 199944705 | 10/1999 |
| AU | A8184698 | 11/1999 |
| AU | 769958 | 2/2000 |
| AU | 199942412 | 2/2000 |
| AU | 760929 B2 | 5/2000 |
| DE | 19517048 C1 | 5/1995 |
| DE | 202005020103 | 6/2006 |
| EP | 843002 A2 | 5/1998 |
| EP | 1284136 A2 | 2/2003 |
| GB | 559089 | 2/1944 |
| JP | 60246306 | 12/1985 |
| JP | 63054345 | 3/1988 |
| JP | 8109104 | 4/1996 |
| JP | 08231335 A | 9/1996 |
| JP | 2001199869 A | 7/2001 |

(Continued)

OTHER PUBLICATIONS

American Journal of Clinical Nutrition, Chapter 1 Introduction, 1988, 1083-1102, 48.
Cosmetic Ingredients from Adina Chemicals, Cosmetic Ingredients from Adina Chemicals, ., ., ., ., US.
Nivea Product Lines, Alpine Village Cosmetics, Dec. 14, 2008, 1-7, ., Alpine Village Cosmetics, US.
Alargova et al., Scalable Synthesis of a New Class of Polymer Microrods by a Liquid-Liquid Disperson Technique, Advanced Materials 2004 16 No. 18 pp. 1653-1657, Sep. 16, 2004, 1653-1657, 16 No. 18.

(Continued)

*Primary Examiner* — Raymond Henley, III
(74) *Attorney, Agent, or Firm* — Edward A. Squlliante, Jr.

(57) ABSTRACT

Stabilized cationic ammonium compounds are described. The compounds are stabilized with pyridine-based chelators and/or heteroketo-based chelators that impede the generation of nitrogen comprising groups from the cationic ammonium compounds.

19 Claims, No Drawings

(56) References Cited

FOREIGN PATENT DOCUMENTS

| | | |
|---|---|---|
| JP | 2001225334 A | 8/2001 |
| JP | 2001226334 A | 8/2001 |
| WO | W09508440 A1 | 3/1995 |
| WO | WO9523521 | 9/1995 |
| WO | WO9702010 A1 | 1/1997 |
| WO | WO9740816 A1 | 11/1997 |
| WO | WO9960082 A1 | 11/1999 |
| WO | WO0100146 A1 | 1/2001 |
| WO | WO0100172 A1 | 1/2001 |
| WO | WO02078661 A2 | 10/2002 |
| WO | WO2006045427 A1 | 5/2006 |
| WO | WO2006061661 A1 | 6/2006 |
| WO | WO2010069770 | 6/2010 |

OTHER PUBLICATIONS

Aveyard, Emulsions stabilised solely by colloidal particles, Advances in Colloid and Interface Science, 2003, 503-546, 100-102, US.
Dujardin et al., Bio-inspired Materials Chemistry, Advanced Materials, Jun. 5, 2002, 775-787, vol. 14, No. 11.
Hagerstrom, Comprehensive Summaries of Uppsala Dissertations from the Faculty of Pharmacy 293, ACTA Universitatis Upsaliensis Uppsala, 2003, 1-76, ., US.
Hunter, et al., The role of particles in stabilising foams and emulsions, Advances in Colloid & Interface Science, Jan. 1, 2008, 57-81, 137.
Pierard-Franchimont, Assessment of aging and actinic damages by cyanoacrylate skin surface strippings, Am J Dermatopathol, Dec. 1, 1987, ., vol. 9—No. 6, Medline, US.
Shafran, High-Temperature Speciation Studies of Al-Ion Hydrolysis**, Advanced Engineering Materials, 2004, 836-839, vol. 6 No. 10, US.
Smart, The basics and underlying mechanisms of mucoadhesion, Advanced Drug Deliver Reviews, 2005, 1556-1568, 57, US.
Southgate, The Relationship Between Food Composition and Available Energy, ARC Food Research Institute, 1981, pp. 4-8, 1, GB.
Sticher, Biochemical Pharmaceutical and Medical Perspectives of Ginseng, Biochemical Pharmaceutical and Medical Perspectives of Ginseng, ., 221-240, 691, American Chemical Society, US.
Stolle-Smits et al, Cell Wall Dissolution during Industrial Processing of Green Beans (*Phaseolus vulgaris* L.), Journal of Agriculture and Food Chemisry, Jan. 1, 1995, 2480-2486, vol. 43.
Vahlquist, Markers of Skinn Inflammation and Wound healing, Acta Derm Venereol, 2000, 161, 80, Taylor & Francis, US.
Van Den Enden, A Method for the Determin of the Solid Phase Content of Fats Using Pulse Nuclear Magnetic Resonance, Fette Seifen Anstrichmittel, 1978, 180, 5, US.
Vlachopoulus et al, Relation of Habittual Cocoa Consumption to Aortic Stiffness and Wave Reflections, American Journal of Cardiology, May 9, 2007, 1473-1475, vol. 99 No. 10.
Wang et al., Phase-Separation-Induced Micropatterned POlymer Surfaces and Their Applications, Advanced Functional Materials, 2005, 655-663, vol. 15—No. 4, CN.
Wessels, Hydrophobins Proteins that Change the Nature of the Fungal Surface, Advances in Microbial Physiology, 1997, 1-45, 38, No. 38, NL.
International Search Report and Written Opinion on Appln. No. PCT/EP2010/063022 dated Aug. 18, 2011.
International Search Report on Appln. No. PCT/EP2010/054090 dated Jul. 30, 2010.
Aluminum oxide, Wikipedia Encyclopedia, 2007, 1-4.
Anselmi, Molecular mechanics conformation analysis, Acta Technologiae et Legis Medicamenti, 1998, 49-67, vol. 9 No. 1.
Anselmi, Sunscreen Agents As Multiactive Ingredients, Active Ingredients Conference Proceedings, 1996, 55-62.
Anselmi, Synthesis, Crystal Structure and Properties of N, N-Dimethyl-N, Acta Technologiae et Legis Medicamenti, 1997, 85-93, vol. 8 No. 2.
Bauer et al., Common Fragrance and Flavor Materials, 1990.
Carvallo, Formulation of an avocado paste product, Alimentos, Jan. 1, 1983, 9-14, 8, No. 4, Fac.de Ingenieria.
Chris Craft Industrial Products, Inc., Detergents Packaged More Safely, European Plastics News—ABS, 1996, 69, 23 5.
Daihachi Chemical Industry Co., Japan Chemical Firms Seeking Ways to Cope with Changing Situation (Part 3), Japan Chemical Week—ABS, 1992'6-7, 33-1675.
Daiichi Kogyo Seiyaku Co., Polyethers for Films, Modem Plastics International—ABS, 1993, 70, 23-5.
Eteng et al., Comparative Effects of Theobromine and Cocoa Extract on Lipid Profile in Rats. Nutrition Research, 2000, 1513-1517, vol. 20 No. 10.
Fauvarque, Ethylene Oxide: Moving Towards Optimum Integration, informations Chimie. 1994, 123-134, 363.
Innis, Key Concepts for PCR, PCR Strategies, 1995, 373 PP, Academic Press, Inc.
Josling, Preventing the Common Cold With a Garlic Supplement, Advances in Therapy, 189-193, vol. 18 No. 4.
Kim, Effect of extracting conditions on chemical compositions of Korean mountain ginseng extract, Journal of the Korean Society of Food Science and Nutrition, 2005, 862-868Abstract, vol. 34 No. 6.
Kokubo, Apatite Formation on Surfaces of Ceramics, Metals and Polymers in Body Environment, Acta Mater., 1998, 2519-2527, vol. 46 No. 7, Elsevier Science Ltd., Great Britain.
Kudou et al., Malonyl lsoflavone Glycosides in Soybean Seeds, Agric. Biol Chem, Jan. 21, 1991; 2227-2233, 55-9, Japan Society for Bioscience, Biotechnology and Agrochemistry.
Li et al., Determination of trimethylamine in fish by capillary electrophoresis with electrogenerated tris(2,2'-hipyridyl) ruthenium(II) chemiluminescence detection, Luminescence, 2007, 583-593, 22.
Libby, Inflammation and Atherosclerosis, American Heart Assocation, Oct. 19, 2010, 1135-1143, vol. 105.
Lopez et al., Growth of hydroxyapatite in a biocompatible mesoporous ordered silica, Acta Biomaterialia, 2006, 173-179, 2, Elsevier.
Martin et al, Micronization processes with supercritical fluids: Fundamentals and mechanisms, Advanced Drug Delivery Reviews, Oct. 11, 2007, 339-350, vol. 60 No. 3.
McCarthy-Bates, Biodegradables Blossom into Field of Dreams for Packagers, Plastics World—ABS, 1993 22-27, 51-3.
McDevitt-Pugh et al., Weigh management supported by tasty inulin-based products, AgroFOOD Industry Hi-tech, Oct. 2005, 1-2, 16(5).
Nakamura, Age-related changes in the protective effect of chronic administration of L-arginine on post-ischemic recovery of endothelial function, European Journal of Cardio-thoracic Surgery, 626-632, 23/4, European Journal of Cardio-thoracic Surgery 6.
Pasare, Toll-Like Receptors: Linking Innate and Adaptive Immunity, Advanced Exp. Medical Biology, 2005, 11-18, 560.
Prabha Polyphenol oxidase and peroxidase enzyme activities in ripening fruits, Acta Alimentana, 1986, 199-207. 15, No. 3, Cent. Food Tech Res. inst., ABS.
Reilly, Inflammatory Mediators in Normal Sensitive and Diseased Skin Types, Acta Derm Venereol, 2000, 171-174, 80, Taylor & Francis.
Renfree et al., Development of a Standard Protocol to Produce Petp Flake for the Evaluation of Possible Discolouration Resulting from Labels, Antec'96, May 5, 1996, 3126-30, III, ABSI.
Yang, Alleviation of brain edema by L-arginine. Alleviation of brain edema by L-arginine, 2003, 437-443, 29, Clinical Hermorheology and Microcirculation, ABS.

* cited by examiner

CHELATOR STABILIZED CATIONIC AMMONIUM COMPOUNDS AND COMPOSITIONS COMPRISING THE SAME

FIELD OF THE INVENTION

The present invention is directed to stabilized cationic ammonium compounds. More particularly, the invention is directed to cationic ammonium compounds stabilized with a pyridine-based chelator, heteroketo-based chelator or both whereby such cationic ammonium compounds, unexpectedly, do not display dealkylation in, for example, an aqueous environment. Such chelators are suitable for use in compositions that are, for example, applied topically and to enhance a skin benefit.

BACKGROUND OF THE INVENTION

Dry skin is often a problem in varying degree to most consumers. This condition is particularly evident in winter. In view of such a problem, personal care products like skin creams, lotions, toilet bars, shower gels and deodorants are normally formulated with at least one material suitable to address dry skin. These products can, to some degree, help in modulating symptoms such as itching, flaking and a displeasing dermal appearance.

Traditional classes of materials used to address dry skin and skin moisturization include occlusives like petrolatum and silicone oils, as well as keratolytic agents such as alpha-hydroxy acids. Other materials traditionally used to improve dry skin conditions are humectants. The substances generally classified as hydroxylated monomeric and polymeric organic substances are the most frequently used for this purpose. Glycerin, also known as glycerine or glycerol, is perhaps the most popular humectant employed in topical compositions.

New trends in skin moisturization have led to the use of quaternary ammonium compounds in topical skin formulations. Preferred quaternary ammonium compounds comprise a trimethyl ammonium group known generally via INCI nomenclature as a trimonium group. While such compounds are preferred for moisturization benefits, they tend to be unstable when, for example, water is present. This instability results in the generation of a nitrogen comprising group from the quaternary ammonium compound (i.e., a dealkylation and release of the characteristic trimonium group) which can produce an unpleasant odor, may diminish the moisturizing efficacy of the compound, or both. The generation of a nitrogen comprising group from the quaternary ammonium compound may also require more intense perfumes or fragrances in end use compositions. Moreover, such generation of a nitrogen comprising group in an end use composition typically requires product to be stored and shipped at cold temperatures so that product longevity may be prolonged.

There is an increasing interest to develop stabilized cationic ammonium compounds for all applications, and especially, applications where skin moisturization is desired. This invention, therefore, is directed to stabilized cationic ammonium compounds. The cationic ammonium compounds are stabilized with a pyridine-based chelator, heteroketo-based chelator or both, and unexpectedly, the generation of a nitrogen comprising group in, for example, an aqueous environment is impeded. Such stabilized compounds are suitable for use in topical applications, including leave-on and wash-off compositions and even applications associated with oral care, laundry care and household care.

ADDITIONAL INFORMATION

Efforts have been disclosed for making personal care compositions with quaternary ammonium compounds. In U.S. Pat. Nos. 7,087,560, 7,176,172 and 7,282,471, compositions with quaternary ammonium salts are described.

Other efforts have been disclosed for making personal care compositions. In U.S. Pat. No. 7,175,836, cosmetic emulsions are described.

Still other efforts have been disclosed for making personal care compositions. In U.S. Patent Application No. 2008/0299054 A1, personal care compositions with enhanced fragrance delivery are described.

None of the additional information above describes cationic ammonium compounds suitable for at least cosmetic applications and having been stabilized with a pyridine-based chelator, heteroketo-based chelator or both.

SUMMARY OF THE INVENTION

In a first aspect, the present invention is directed to compositions comprising a cationic ammonium compound and a pyridine-based chelator, heteroketo-based chelator or both, the chelator being one which impedes the generation of a nitrogen comprising group from the cationic ammonium compound within the composition.

In a second aspect, the present invention is directed to a composition comprising a cationic ammonium compound having the formula:

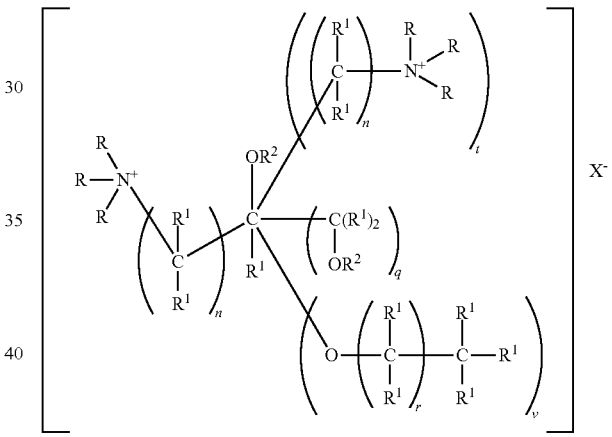

wherein q, t and v are each independently 0 or 1 with the proviso that the sum of q, t and v is equal to 1, each R is independently hydrogen, $C_{1-12}$ alkyl, $C_{1-12}$ hydroxy alkyl or

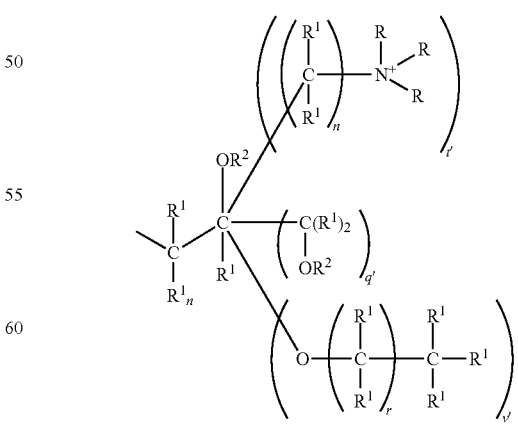

where q', t' and v' are each independently 0 or 1 with the proviso that the sum of q', t' and v' is equal to 1, each $R^1$ is independently a hydrogen, $C_{1-12}$ alkyl, or a $C_{1-12}$ hydroxy alkyl, each $R^2$ is independently hydrogen, $C_{1-3}$ alkyl, monosaccharyl, oligosaccharyl or polysaccharyl, each n is independently an integer from 1 to about 12, r is an integer from 0 to about 5, $X^-$ is an anionic counterion, the cationic ammonium compound being stabilized with a pyridine based chelator, a heteroketo-based chelator, or both.

In a third aspect, the present invention is directed to an end use composition comprising the composition with cationic ammonium compound of the first aspect of this invention.

In a fourth aspect, the present invention is directed to a method for stabilizing a cationic ammonium compound.

All other aspects of the present invention will more readily become apparent upon considering the detailed description and examples which follow.

End use composition, as used herein, is meant to include a substance applied to a human body for improving appearance, cleansing, odor control and/or general aesthetics. Illustrative yet non-limiting examples include leave-on skin lotions and creams, shampoos, hair conditioners, shower gels, toilet bars, antiperspirants, deodorants, dental products, shaving creams, depilatories, lipsticks, foundations, mascara, sunless tanners and sunscreen lotions. End use composition is also meant to include a product associated with oral care, or laundry care or household care such as laundry detergents, fabric conditioners or hard surface cleaners. In a preferred embodiment, however, the end use composition is one which is applied to the human body, and especially, topically to skin. Stabilized, as used herein, means impeding the generation of a nitrogen comprising group such as an amine, a trimonium group and/or ammonia, especially in an aqueous environment.

Comprising, as used herein, is meant to include consisting essentially of and consisting of: All ranges identified herein are meant to implicitly include all ranges subsumed therein, if, for example, reference to the same is not explicitly made.

DETAILED DESCRIPTION OF THE PREFERRED EMBODIMENTS

The only limitation with respect to the cationic ammonium compounds that may be employed in this invention is that the same can be used in a consumer product, and preferably, a topical skin product.

Preferred cationic ammonium compounds that may be stabilized according to this invention have the formula:

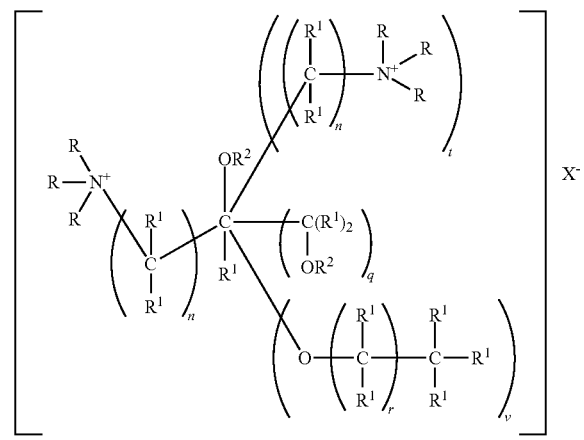

wherein q, t and v are each independently 0 or 1 with the proviso that the sum of q, t and v is equal to 1, each R is independently hydrogen, $C_{1-12}$ alkyl, $C_{1-12}$ hydroxy alkyl or

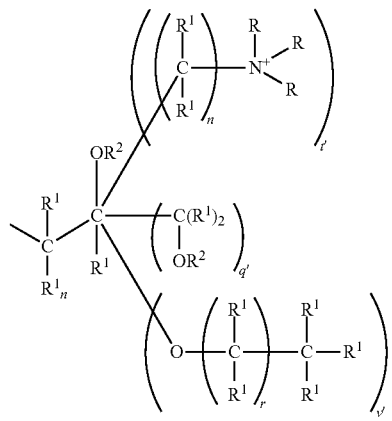

where q', t' and v' are each independently 0 or 1 with the proviso that the sum of q', t' and v' is equal to 1, each $R^1$ is independently a hydrogen, $C_{1-12}$ alkyl, or a $C_{1-12}$ hydroxy alkyl, each $R^2$ is independently hydrogen, $C_{1-3}$ alkyl, monosaccharyl, oligosaccharyl or polysaccharyl, each n is independently an integer from 1 to about 12, r is an integer from 0 to about 5, and $X^-$ is an anionic counterion.

The anionic counterions used herein can be organic or inorganic and must be cosmetically acceptable when the end use composition is applied to the body. Illustrative examples of such inorganic anionic counterions include halides (especially, chlorine), sulfates, phosphates, nitrates and borates. Organic anionic counterions include methosulfate, toluoyl sulfate, acetate, citrate, tartrate, lactate, gluconate and benzosulfonate. Optionally, a portion of such organic anionic counterion can comprise the chelator defined herein. Polysaccharyl is meant to include a gum suitable for use in a topical composition, oral care product, and/or a laundry care or household care product and including, for example, cellulose, xanthan, agar, carrageenan, galactamannans like guar and/or locus bean gum (all of which can form radicals to form part of an ether link to the quaternary ammonium compound). Preferred monosaccharyls (i.e., simple sugars) include glucosyl, fructosyl, galactosyl, xylosyl and ribosyl. Oligosaccharyls are meant to include disaccharyls where by the same can be sucrosyl, trehalosyl, lactosyl, maltosyl, or cellubiosyl as well as fructo- or galactoologosaccharyl.

Often preferred cationic ammonium compounds suitable for use herein include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment, the cationic ammonium compound employed in this invention is the quaternary ammonium compound 1,2-dihydroxypropyl-trimonium chloride.

Such a cationic ammonium compound is, unexpectedly, stabilized with a pyridine-based chelator, heteroketo-based chelator or both that impede(s) the generation of a trimonium group. Typically, the composition comprising cationic ammonium compound and chelator comprises from about 0.0001 to about 10%, and preferably, from about 0.01 to about 8%, and most preferably, from about 0.01 to about 5% by chelator, based on total weight of cationic ammonium compound and chelator, and including all ranges subsumed therein. While the cationic ammonium compound described herein may be supplied in an anhydrous (i.e., alcohol) solution or powder, in an especially preferred embodiment, the cationic ammonium compound is supplied as an aqueous solution comprising from about 10 to about 90%, and preferably, from about 20 to about 85%, and most preferably, from about 40 to about 75% by weight water, based on total weight of the aqueous solution and including all ranges subsumed therein. End use compositions comprising the composition with stabilized cationic ammonium compound typically comprises from about 0.02 to about 30%, and preferably, from about 0.1 to about 25%, and most preferably, from about 5 to about 18% by weight cationic ammonium compound, based on total weight of the end use composition and including all ranges subsumed therein.

The preferred cationic ammonium compounds suitable for use in this invention may be made via art recognized techniques. For example, the same may be made by reacting primary halo-dihydroxy alkanes and trialkylamines in a stoichiometric excess followed by excess removal and a pH reduction in order to recover the desired cationic ammonium compound. Other techniques and compounds are described in U.S. Patent Application Nos. 2007/0212324 A1, and 2007/0299284 A1, as well as U.S. Pat. Nos. 7,176,172 B2 and 7,282,471 B2, the disclosures of which are incorporated herein by reference.

The cationic ammonium compounds suitable for use in this invention can be commercially available. Suppliers of the same include Dow Chemical, HallStar, Rhodia Group, Colonial Chemical Company as well as Evonik Degussa.

Chelators suitable for use in this invention preferably comprise pyridine based and/or heteroketo-based components. In a most preferred embodiment, the chelators suitable for use comprise groups that are represented by the formulae:

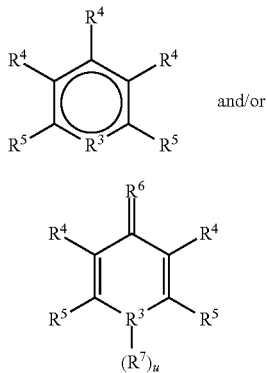

and/or wherein:
each $R^3$ is independently N or O and each u is 0 or 1 with the proviso that u is not 1 when $R^3$ is O;
each $R^4$ is independently H, OH, $NH_2$,

where D is
H or a cation selected from the group consisting of Na, K, Li, Ca, Mg or $N(R^8)_4$
where each $R^8$ is independently H or a $C_{1-3}$ alkyl;
each $R^5$ is independently

where each Z independently H, $C_{1-3}$ alkyl $N(R^8)_2$, OD, aryl
or

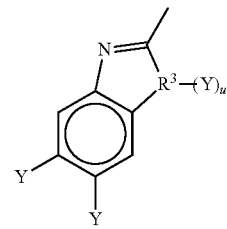

where each Y is independently H, OH, a $C_{1-6}$ alkyl or aryl, and each $Z^1$ is independently O or N—Y;
$R^6$ is O or N—Y; and
$R^7$ is H or a $C_{1-6}$ alkyl.

In an especially preferred embodiment, the chelator used in this invention is represented by formula II and is Chelidamic acid (1,4-dihydro-4-oxo-2,6-pyridinedicarboxylic acid). Chelator typically makes up from about 0.01 to about 7%, and preferably, from about 0.03 to about 4%, and most preferably, from about 0.03 to about 3.5% by weight of the total weight of the end use composition, including all ranges subsumed therein.

The chelators suitable for use herein may be made commercially available from suppliers like Sigma-Aldrich, as well as Alfa Aesar GmBh.

End use compositions of this invention will preferably include a cosmetically acceptable carrier. Amounts of the carrier may range from about 1 to about 99.9%, preferably from about 70 to about 95%, optimally from about 80 to about 90% by weight of the composition. Among the useful carriers are water, emollients, fatty acids, fatty alcohols, thickeners and combinations thereof. The carrier may be aqueous, anhydrous or an emulsion. Preferably the end use compositions are aqueous, especially water and oil emulsions of the W/O or O/W or triplex W/O/W variety. Water, when present, may be in amounts ranging from about 5 to about 95%, preferably from about 20 to about 70%, optimally from about 35 to about 60% by weight of the end use composition.

Emollient materials may serve as cosmetically acceptable carriers. These may be in the form of silicone oils, natural or synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to $0.1$ $m^2/s$ at 25° C. Among the preferred nonvolatile emollients useful in the present end use composition are the polydimethyl siloxanes having viscosities from about $1 \times 10^{-5}$ to about $4 \times 10^{-4}$ $m^2/s$ at 25° C.

Another class of nonvolatile silicones are emulsifying and non-emulsifying silicone elastomers. Representative of this category is Dimethicone/Vinyl Dimethicone Crosspolymer available as Dow Corning 9040 and Shin-Etsu KSG-18. Silicone waxes such as Silwax WS-L (Dimethicone Copolyol Laurate) may also be useful.

Among the ester emollients are:
a) Alkyl esters of saturated fatty acids having 10 to 24 carbon atoms. Examples thereof include behenyl neopentanoate, isononyl isonanonoate, isopropyl myristate and octyl stearate.
b) Ether-esters such as fatty acid esters of ethoxylated saturated fatty alcohols.
c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.
d) Wax esters such as beeswax, spermaceti wax and tribehenin wax,
e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the end use compositions.

Hydrocarbons which are suitable cosmetically acceptable carriers include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol.

Thickeners can be utilized as part of the cosmetically acceptable carrier of end use compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Metal chelators, like diethylenetriaminepentacetic acid (DTPA), triethylenetetraaminehexacetic acid, hexamethylenediaminetetramethylenehexacetic acid or mixtures thereof may be used along with the preferred pyridine-based and/or heteroketo-based chelators of this invention. Such metal chelators, if used, can make up from about 1 to about 45% by weight of the total weight of chelator employed in the end use composition of this invention.

Adjunct humectants may be employed in the present invention. These are generally polyhydric alcohol-type materials. Typical polyhydric alcohols include glycerol, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from 0.5 to 50%, preferably between 1 and 15% by weight of the composition.

Surfactants may also be present in end use compositions of the present invention. Total concentration of the surfactant when present may range from about 0.1 to about 90%, preferably from about 1 to about 40%, optimally from about 1 to about 20% by weight of the composition, and being highly dependent upon the type of personal care product. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Useful amphoteric surfactants include cocoamidopropyl betaine, $C_{12}$-$C_{20}$ trialkyl betaines, sodium lauroamphoacetate, and sodium laurodiamphoacetate.

Perfumes may be used in the topical composition of this invention. Illustrative non-limiting examples of the types of perfumes that may be used include those comprising terpenes and terpene derivatives like those described in Bauer, K., et al., *Common Fragrance and Flavor Materials*, VCH Publishers (1990).

Illustrative yet non-limiting examples of the types of fragrances that may be used in this invention include myrcene, dihydromyrenol, citral, tagetone, cis-geranic acid, citronellic acid, mixtures thereof or the like.

Preferably, the amount of fragrance employed in the topical composition of this invention is in the range from about 0.0% to about 10%, more preferably, about 0.00001% to about 5 wt %, most preferably, about 0.0001% to about 2%. Moreover, since the present invention yields less nitrogen comprising groups, more fragrance options are available and high note fragrances are not required and may be replaced with enduring perfumes.

Sunscreen agents may also be included in end use compositions of the present invention. Particularly preferred are such materials as ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide and zinc oxide. Amounts of the sunscreen agents when present may generally range from 0.1 to 30%, preferably from 2 to 20%, optimally from 4 to 10% by weight of the end use composition.

Antiperspirants and deodorant compositions of the present invention ordinarily will contain astringent actives. Examples include aluminum chlorohydrate, aluminum chlorhydrex, aluminum-zirconium chlorhydrex glycine, aluminum sulfate, zinc sulfate, zirconium and aluminum chlorohydroglycinate, zirconium hydroxychloride, zirconium and aluminum lactate, zinc phenolsulfonate and combinations thereof. Amounts of the astringents may range anywhere from about 0.5 to about 50% by weight of the end use composition.

Oral products formulated according to the present invention will generally contain a fluoride source to prevent dental caries. Typical anti-caries actives include sodium fluoride, stannous fluoride and sodium monofluoro phosphate. Amounts of these materials will be determined by the amount of fluoride releasable which should range between about 500 to about 8800 ppm of the composition. Other components of dentifrices can include desensitizing agents such as potassium nitrate and strontium nitrate, sweeteners such as sodium saccharine, aspartame, sucralose, and potassium acesulfam. Thickeners, opacifying agents, abrasives and colorants will normally also be present.

Preservatives can desirably be incorporated into the end use compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.01% to 2% by weight of the end use composition.

End use compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the end use composition.

Another type of useful substance can be that of an enzyme such as amylases, oxidases, proteases, lipases and combinations. Particularly preferred is superoxide dismutase, commercially available as Biocell SOD from the Brooks Company, USA.

Skin lightening compounds may be included in the compositions of the invention. Illustrative substances are placental extract, lactic acid, niacinamide, arbutin, kojic acid, ferulic acid, 12-hydroxystearic acid, resorcinol and derivatives including 4-substituted resorcinols and combinations thereof. Amounts of these agents may range from about 0.1 to about 10%, preferably from about 0.5 to about 2% by weight of the endues composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the end use composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary.

Also included may be such materials as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the end use composition.

Colorants, opacifiers and abrasives may also be included in the end use compositions of the present invention. Each of these substances may range from about 0.05 to about 5%, preferably between 0.1 and 3% by weight of the composition.

Especially preferred additives suitable for use with the stabilized quaternary ammonium compounds of this invention are moisturizing agents such as substituted ureas like hydroxymethyl urea, hydroxyethyl urea, hydroxypropyl urea; bis(hydroxymethyl)urea; bis(hydroxyethyl)urea; bis (hydroxypropyl)urea, N,N'-dihydroxymethyl urea; N,N'-dihydroxyethyl urea; N,N'-di-hydroxypropyl urea; N,N,N'-trihydroxyethyl urea; tetra(hydroxymethyl)urea; tetra (hydroxyethyl)urea, tetra(hydroxypropyl urea; N-methyl, N'-hydroxyethyl urea; N-ethyl-N'-hydroxyethyl urea; N-hydroxypropyl-N'-hydroxyethyl urea and N,N'dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the end use composition of this invention range from about 0.01 to about 20%, and preferably, from about 0.5 to about 15%, and most preferably, from about 2 to about 10% based on total weight of the end use composition and including all ranges subsumed therein.

When stabilized ammonium compound and substituted urea are used, in a most especially preferred embodiment at least from about 0.01 to about 25%, and preferably, from about 0.2 to about 20%, and most preferably, from about 1 to about 15% humectant, like glycerine, is used, based on total weight of the end use composition and including all ranges subsumed therein.

A wide variety of packaging can be employed to store and deliver the end use compositions. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

End use compositions of the present invention may be in any form. These forms may include lotions, creams, roll-on formulations, sticks, mousses, aerosol and non-aerosol sprays and fabric (e.g. nonwoven textile)-applied formulations.

The following examples are provided to facilitate an understanding of the present invention. The examples are not intended to limit the scope of the claims.

Example 1

Aqueous Solutions comprising circa 50% by weight water and 50% by weight dihydroxypropyltrimonium chloride were combined with about 0.12% by weight chelator and stirred to yield a homogeneous solution. The solutions were stored at 25° C. for periods of up to two (2) months. Trimonium group generation (i.e., trimethylamine) was monitored and such monitoring may be achieved with known methods employing, for example, gas chromatography-mass spectroscopy or capillary electrophoresis with electrogenerated chemiluminescence.

| 50% Quaternary Ammonium Compound Solution* | Chelator | Temperature (° C.) | Rate of Trimethylamine Generation** PPM/Day |
|---|---|---|---|
| 1 | DTPA | 25 | 0.0014 |
| 2 | Control | 25 | 0.02 |
| 3 | Chelidamic acid | 25 | 0.0009 |

*Commercially available from Dow Chemical.
**Determined using the formula - Rate of Trimethylamine Generation = (Rate of Trimethylamine generation with chelators/Rate of Trimethylamine generation without chelator) × 100.

The results indicate that compositions made according to this invention unexpectedly generate about 20 times less trimethylamine per day than compositions deplete of pyridine-based chelator of this invention and stored at the same temperature.

Example 2

Control and chelator comprising solutions similar to the ones above were made. The solutions were stored at 50° C. for about one (1) month. Assessment, after storage, revealed that after about twenty (20) days, the chelidamic acid comprising solution had about 40% less trimethylamine than the control. After about one (1) month, the solution with chelidamic acid had about 50% less trimethylamine than the control.

What is claimed is:
1. A composition comprising a cationic ammonium compound and a pyridine-based chelator, a heteroketo-based chelator, or both, the chelator being one which impedes the generation of a nitrogen comprising group from the cationic ammonium compound within the composition wherein the nitrogen comprising group comprises a trimonium group.

2. A composition comprising a cationic ammonium compounds having the formula:

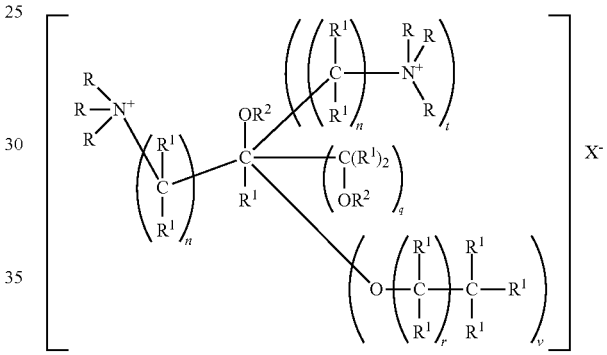

wherein q, t and v are each independently 0 or 1 with the proviso that the sum of q, t and v is equal to 1, each R is independently hydrogen, $C_{1-12}$ alkyl, $C_{1-12}$ hydroxy alkyl or where q', t' and v' are each independently 0 or 1 with the proviso that the sum of q', t' and v' is equal to 1, each $R^1$ is independently a hydrogen, $C_{1-12}$ alkyl, or a $C_{1-12}$ hydroxy alkyl, each $R^2$ is independently hydrogen, $C_{1-3}$ alkyl, monosaccharyl, oligosaccharyl or polysaccharyl, each n is independently an integer from 1 to about 12, r is an integer from 0 to about 5, $X^-$ is an anionic counterion, the cationic ammonium compound being stabilized with a chelator, comprising pyridine-based chelator, heteroketo-based chelator or both.

3. The composition according to claim 2 wherein the anionic counterion is organic or inorganic.

4. The composition according to claim 2 wherein the chelator comprises groups represented by the formulae

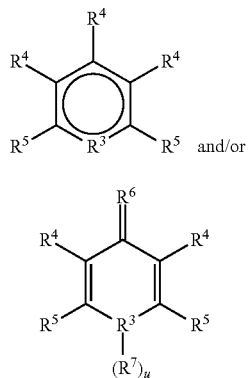

wherein:
each $R^3$ is independently N or O and each u is 0 or 1 with the proviso that u is not 1 when $R^3$ is O;
each $R^4$ is independently H, OH, $NH_2$, $NO_2$,

where D is
H or a cation selected from the group consisting of Na, K, Li, Ca, Mg or $N(R^8)_4$
where each $R^8$ is independently H or a $C_{1-3}$ alkyl;
each $R^5$ is independently

where each Z independently H, $C_{1-3}$ alkyl $N(R^8)_2$, OD, aryl
or

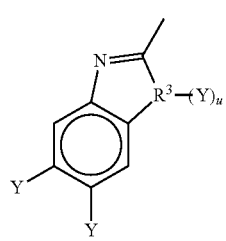

where each Y in independently H, OH, a $C_{1-6}$ alkyl or aryl, and each $Z^1$ is independently
O or N—Y;
$R^6$ is O or N—Y; and
$R^7$ is H or a $C_{1-6}$ alkyl.

5. The composition according to claim 2 wherein the cationic ammonium compound is a salt of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof.

6. The composition according to claim 2 wherein the cationic ammonium compound is 1,2-dihydroxypropyltrimonium chloride.

7. A composition comprising:
(a)

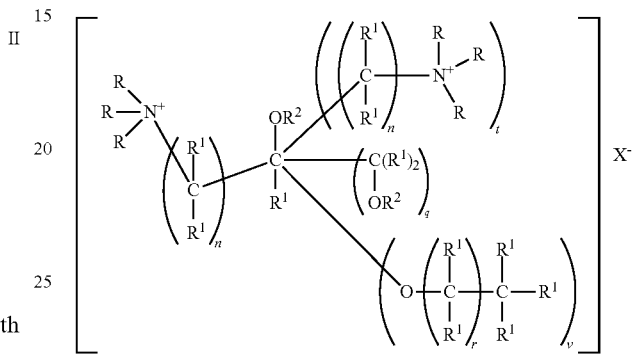

(b) a cosmetically acceptable carrier; and
(c) a preservative wherein q, t and v are each independently 0 or 1 with the proviso that the sum of q, t and v is equal to 1, each R is independently hydrogen, $C_{1-12}$ alkyl, $C_{1-12}$ hydroxy alkyl or

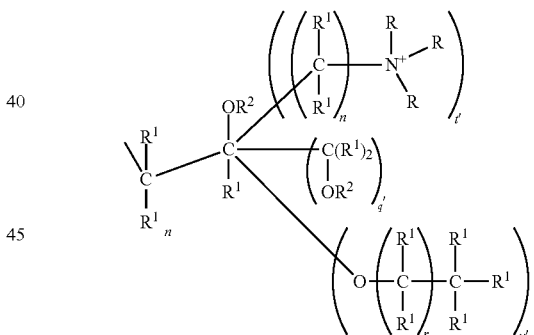

where q', t' and v' are each independently 0 or 1 with the proviso that the sum of q', t' and v' is equal to 1, each $R^1$ is independently a hydrogen, $C_{1-12}$ alkyl, or a $C_{1-12}$ hydroxy alkyl, each $R^2$ is independently hydrogen, $C_{1-3}$ alkyl, monosaccharyl, oligosaccharyl or polysaccharyl, each n is independently an integer from 1 to about 12, r is an integer from 0 to about 5, $X^-$ is an anionic counterion, the cationic ammonium compound being stabilized with a chelator comprising pyridine-based chelator, heteroketo-based chelator, or both.

8. The composition according to claim 7 wherein the composition is topically applied to the body.

9. The composition according to claim 8 wherein the composition is a leave-on or rinse off composition.

10. The composition according to claim 9 wherein the composition is a moisturizing composition.

11. The composition according to claim 9 wherein the cationic ammonium compound is a salt of a hydroxypropyltri (C$_1$-C$_3$ alkyl) ammonium mono-substituted saccharide, salts of hydroxypropyltri (C$_1$-C$_3$ alkyl) ammonium mono-substituted polyols, dihydroxypropyltri (C$_1$-C$_3$ alkyl) ammonium salts, dihydroxypropyldi (C$_1$-C$_3$ alkyl) mono(hydroxyethyl) ammonium salts, guar hydroxypropyl trimonium salts, 2,3-dihydroxypropyl tri(C$_1$-C$_3$ alkyl or hydroxalkyl) ammonium salts or mixtures thereof.

12. The composition according to claim 8 wherein the cationic ammonium compound is 1,2-dihydroxypropyltrimonium chloride.

13. The composition according to claim 9 wherein the composition comprises from about 0.02 to about 30% by weight cationic ammonium compound and from about 0.01 to about 7% by weight chelator.

14. The composition according to claim 9 wherein the chelator comprises groups represented by the formulae

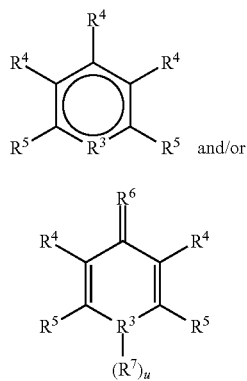

wherein:
each R$^3$ is independently N or O and each u is 0 or 1 with the proviso that u is not 1 when R$^3$ is O;
each R$^4$ is independently H, OH, NH$_2$, NO$_2$,

where D is
H or a cation selected from the group consisting of Na, K, Li, Ca, Mg or N(R$^8$)$_4$
where each R$^8$ is independently H or a C$_{1-3}$ alkyl;
each R$^5$ is independently

were each Z independently H, C$_{1-3}$ alkyl N(R$^8$)$_2$, OD, aryl
or

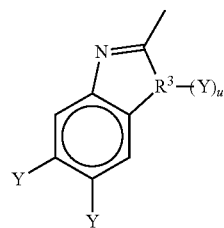

where each Y in independently H, OH, a C$_{1-6}$ alkyl or aryl, and each Z$^1$ is independently
O or N—Y:
R$^6$ is O or N—Y; and
R$^7$ is H or a C$_{1-6}$ alkyl.

15. The composition according to claim 9 wherein the chelator is chelidamic acid.

16. The composition according to claim 9 wherein the composition further comprises a humectant.

17. The composition according to claim 9 wherein the composition further comprises a substituted urea.

18. The composition according to claim 16 wherein the humectant is glycerine.

19. A method for stabilizing a cationic ammonium compound comprising the steps of:
a) contacting the cationic ammonium compound with a pyridine-based chelator and/or a heteroketo-based chelator; and
b) impeding the formation of a nitrogen comprising group wherein the nitrogen comprising group comprises a trimonium group.

* * * * *